United States Patent
Kim et al.

(10) Patent No.: US 9,554,983 B2
(45) Date of Patent: Jan. 31, 2017

(54) HYDROPHILIC SILICON PARTICLES WITH IMPROVED HEAT-RESISTANCE AND TOUCH FEELING AND METHODS FOR PREPARAING THE SAME

(71) Applicant: NANO AND MICRO TECHNOLOGIES CO., LTD., Daejeon (KR)

(72) Inventors: Ji-Woong Kim, Daejeon (KR); Jin Seong Park, Seoul (KR); Young Baek Kim, Daejeon (KR)

(73) Assignee: NANO AND MICRO TECHNOLOGIES CO., LTD., Daejeon (KR)

( * ) Notice: Subject to any disclaimer, the term of this patent is extended or adjusted under 35 U.S.C. 154(b) by 0 days.

(21) Appl. No.: 14/426,827

(22) PCT Filed: Sep. 24, 2013

(86) PCT No.: PCT/KR2013/008543
§ 371 (c)(1),
(2) Date: Jun. 22, 2015

(87) PCT Pub. No.: WO2014/046520
PCT Pub. Date: Mar. 27, 2014

(65) Prior Publication Data
US 2015/0290113 A1 Oct. 15, 2015

(30) Foreign Application Priority Data

Sep. 24, 2012 (KR) .................... 10-2012-0105962

(51) Int. Cl.
*C08L 83/06* (2006.01)
*A61K 8/891* (2006.01)
(Continued)

(52) U.S. Cl.
CPC ............... *A61K 8/891* (2013.01); *A61K 8/022* (2013.01); *A61K 8/0233* (2013.01);
(Continued)

(58) Field of Classification Search
CPC ............. C08L 83/06; A61K 8/06; A61K 8/84; A61K 2800/621; A61K 2800/654; A61K 8/29; A61K 8/891; A61K 8/0233; A61K 8/022; A61K 8/25; C08G 77/00; C08G 77/04; C01B 33/18; A61Q 19/00; C07F 7/045; C07F 7/1836; C09D 183/06; B01J 13/00
See application file for complete search history.

(56) References Cited

U.S. PATENT DOCUMENTS 5,378,788 A 1/1995 Omura et al.
2008/0118537 A1* 5/2008 Wang .................... A61K 8/891
424/401

FOREIGN PATENT DOCUMENTS

EP 0 444 633 9/1991
KR 10-2004-0108258 12/2004

OTHER PUBLICATIONS

International Search Report for International Application No. PCT/KR2013/008543, dated Dec. 16, 2013.

* cited by examiner

*Primary Examiner* — Carlos Azpuru
(74) *Attorney, Agent, or Firm* — Kile Park Reed & Houtteman PLLC

(57) ABSTRACT

The present invention is related to hydrophilic silicone powders and the methods to prepare the same that contain 1-30 mol % of units selected from a group consisting of (a) partially hydrolyzed silsesquioxane containing one hydroxyl group (T2) and silica (Q3), (b) partially hydrolyzed silsesquioxane containing two hydroxyl groups (T1) and silica
(Continued)

(Q3), (c) silica containing three hydroxyl groups (Q1), hydrolyzed silicone containing siloxane (D1), and mixtures thereof, and hydrophilic silicone powders consisting of core described above and shells composed of silica, and/or titanium dioxide. The particles are useful as ingredients for cosmetics and emulsions because they have good heat resistance, good touching feeling, and readily disperse in water due to their hydrophilic nature and high water absorbency.

5 Claims, 5 Drawing Sheets

(51) Int. Cl.
| | |
|---|---|
| *C01B 33/18* | (2006.01) |
| *B01J 13/02* | (2006.01) |
| *C09D 183/06* | (2006.01) |
| *C07F 7/04* | (2006.01) |
| *C07F 7/18* | (2006.01) |
| *A61K 8/02* | (2006.01) |
| *A61K 8/06* | (2006.01) |
| *A61K 8/25* | (2006.01) |
| *A61K 8/29* | (2006.01) |
| *A61K 8/84* | (2006.01) |
| *A61Q 19/00* | (2006.01) |
| *C08G 77/00* | (2006.01) |
| *C08G 77/04* | (2006.01) |
| *A61K 8/58* | (2006.01) |
| *C08G 77/16* | (2006.01) |

(52) U.S. Cl.
CPC ............ *A61K 8/0279* (2013.01); *A61K 8/06* (2013.01); *A61K 8/25* (2013.01); *A61K 8/29* (2013.01); *A61K 8/585* (2013.01); *A61K 8/84* (2013.01); *A61Q 19/00* (2013.01); *B01J 13/02* (2013.01); *C01B 33/18* (2013.01); *C07F 7/045* (2013.01); *C07F 7/1836* (2013.01); *C08G 77/00* (2013.01); *C08G 77/04* (2013.01); *C08L 83/06* (2013.01); *C09D 183/06* (2013.01); *A61K 2800/10* (2013.01); *A61K 2800/621* (2013.01); *A61K 2800/654* (2013.01); *C08G 77/16* (2013.01)

HYDROPHILIC SILICON PARTICLES WITH IMPROVED HEAT-RESISTANCE AND TOUCH FEELING AND METHODS FOR PREPARAING THE SAME

BACKGROUND OF THE INVENTION

1. Field of the Invention

The present invention is related to silicone powders and the method preparing the same that do not contain thermally degradable component to give non-deforming and no deteriorating powders.

2. Description of the Related Art

Silicon oligomers, polymers or resins are commonly used in cosmetics and various industrial coatings in forms of insoluble powders, soluble powders, soluble liquid with high viscosity, and oligomeric liquid with low viscosity. To summarize, silicone compounds are classified as solid and liquid based on their physical status and soluble and insoluble materials according to their solubility.

Most silicone compounds lack hydrophilicity. Hydrophilic silicone compounds are prepared by combining oligomeric ethylene glycol ad silicone, or by coating hydrophilic polymer on the pre-existing silicone materials. In specific example of polymethylsilsesquioxane, hydrophilic powders are prepared by coating hydrophilic ethylene glycol on the surface of polymethylsilsesquioxane. Such hydrophilic polymethylsilsesquioxane are susceptible to deterioration by heat or under harsh conditions due to organic polymers on the surface. Also the preparation procedure for the preparation such powders is complicated.

Hydrophilic silicone are highly demanded material in various fields including cosmetics in order to develop new formula and new applications. Silica, mica, talc, polymethylsilsesquioxane powders coated with hydrophilic polymer, starch, zinc oxide, titanium dioxide, and iron oxides are examples of currently available hydrophilic powders.

However, these materials do not feel soft on skin and do not spread on skin easily. These materials are often used after modifying their surfaces with organic compounds except polymethylsilsesquioxane, mica, and talc. Some particles still have poor properties even after they are treated with organic compounds. There are few examples of hydrophilic powders with good touching feeling and hydrophilic nature. Especially, there is no example of silicone powder with good touching feeling, heat resistance, and hydrophilic nature.

One of the most required properties for powders to be used in cosmetic properties is good touching feeling. Also the compatibility with other ingredients in cosmetics is highly demanding while powders that swell by specific components in the cosmetics is not desired.

Powders provide different touching feelings according to their sizes, therefore hydrophilic powders with different sizes are highly demanding to prepare various cosmetic formula.

Throughout the specification, a number of publications and patent documents are referred to and cited. The disclosure of the cited publications and patent documents is incorporated herein by reference in its entirety to more clearly describe the state of the related art and the present disclosure.

SUMMARY OF THE INVENTION

The inventors of the present invention have made efforts to prepare powders based on silicone that have good heat resistance, water absorbency, hydrophilicity, good touching feeling, and different sizes. As a result, they have prepared hydrophilic silicone powders of different sizes by inducing partially hydrolyzed silica Q1, Q2, Q3, partially hydrolyzed silsesquioxane T1, T2, partially hydrolyzed siloxane D1 to form near the surface of powders. They have found these powders have good heat resistance because they contain heat resisting silicone, hydrolyzed silicone. They also found that these powders have better touching feeling that hydrophobic polymethylsilsesquioxane that is known to have the best touching feeling. Also, these powders are compatible with different ingredients used in cosmetics.

Accordingly, the present invention is directed to providing hydrophilic silicone powders.

The present invention is also directed to providing core-shell powders consisting of hydrophilic silicone powders core and shells on the surface of the cores.

The present invention is also directed to providing a method for preparing hydrophilic silicone powders.

The present invention is also directed to providing a method for preparing hydrophilic core-shell powders.

The present invention is also directed to providing cosmetic composition containing hydrophilic silicone powder and/or core-shell powders.

The present invention is also directed to providing o/w and w/o emulsion prepared using hydrophilic silicone powders and/or core-shell powders.

The present invention is also directed to providing a method for preparing o/w and w/o emulsion prepared using hydrophilic silicone powders and/or core-shell powders.

Other objects and advantages of the present invention will become apparent from the detailed description to follow taken in conjugation with the appended claims and drawings.

DETAILED DESCRIPTION OF THIS INVENTION

Figure 1:
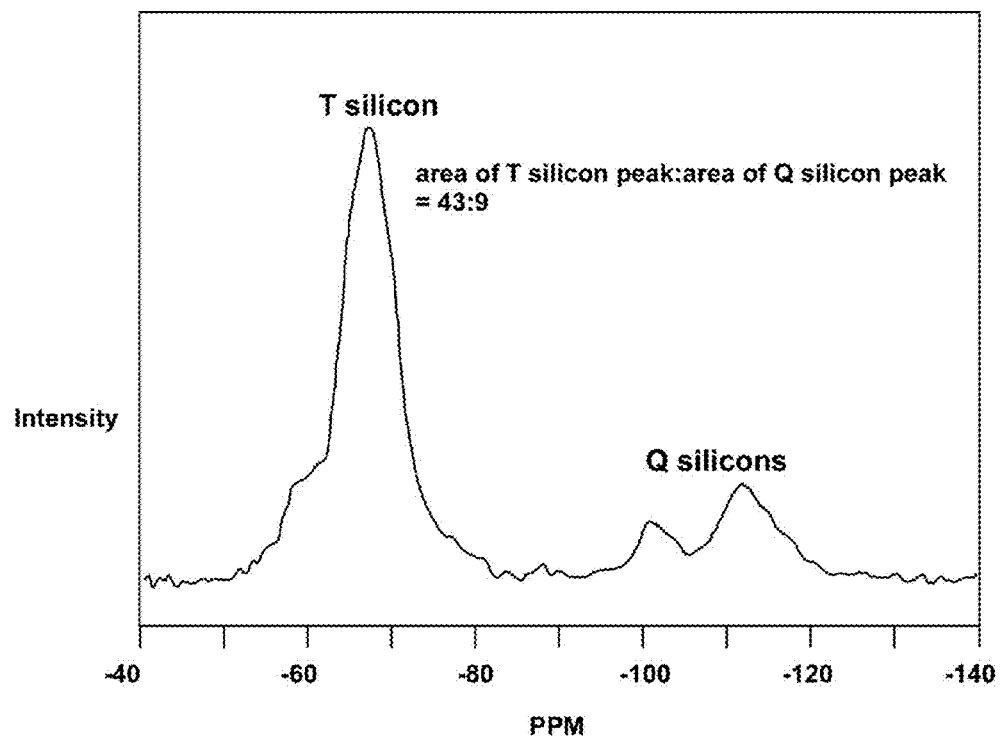
FIG. 1 is a solid state $^{29}$Si NMR spectrum of powder obtained in Example 2.

In one aspect, the present invention provides hydrophilic silicone powders containing 1-30 mol % of units selected from a group consisting of (a) partially hydrolyzed silsesquioxane containing one hydroxyl group (T2) and silica (Q3), (b) partially hydrolyzed silsesquioxane containing two hydroxyl groups (T1) and silica (Q3), (c) silica containing three hydroxyl groups (Q1), hydrolyzed silicone containing siloxane (D1), and mixtures thereof.

In another aspects, the present invention provides core-shell powders consisting of hydrophilic core described above and silica, hydroxyl silica, and titanium dioxide shell.

The inventors of the present invention have made efforts to prepare powders based on silicone that have good heat resistance, water absorbency, hydrophilicity, good touching feeling, and different sizes. As a result, they have prepared hydrophilic silicone powders of different sizes by inducing partially hydrolyzed silica Q1, Q2, Q3, partially hydrolyzed silsesquioxane T1, T2, partially hydrolyzed siloxane D1 to form near the surface of powders. They have found these powders have good heat resistance because they contain heat resisting silicone, hydrolyzed silicone. They also found that these powders have better touching feeling that hydrophobic polymethylsilsesquioxane that is known to have the best touching feeling. Also, these powders are compatible with different ingredients used in cosmetics.

As used herein, the term "core-shell powder" refers to powders consisting of shell material on the surface is entrapping inner core.

As used herein, the term "oil absorbency" refers to a percentage calculated by dividing the minimum weight of oil such as soy bean oil and flaxseed oil used to wet the powder completely by the weight of powder.

As used herein, the term "water absorbency" refers to the same as "oil absorbency" determined using water instead of oil. For example, powders with 100% water absorbency do not flow until 100% of water is added to the powder. The powder start to flow when more than 100% of water is added to the powder.

In an exemplary embodiment of the present invention, the hydrophilic silicone powder in this invention contain 1-25 mol % of units selected from a group consisting of (a) partially hydrolyzed silsesquioxane containing one hydroxyl group (T2) and silica (Q3), (b) partially hydrolyzed silsesquioxane containing two hydroxyl groups (T1) and silica (Q3), (c) silica containing three hydroxyl groups (Q1), hydrolyzed silicone containing siloxane (D1), and mixtures thereof on the surface, more specifically 1-22 mole %, and most specifically 1-20 mol %.

In an exemplary embodiment of the present invention, the hydroxyl group in this invention is produced by hydrolysis by basic solution.

The bases used to produce hydroxyl group in this invention may be NaOH, KOH, Ca(OH)2, Ba(OH), CsOH, Sr(OH)2, LiOH, RbOH, Mg(OH)2, triethylamine, or ammonia. More specifically, the bases are strong inorganic base, and further more specifically NaOH or KOH, and most specifically NaOH.

In an exemplary embodiment of the present invention, the powders in this invention have diameter of 0.1-15 um and more specifically 0.1-12 um.

In an exemplary embodiment of the present invention, the silsesquioxane in this invention are polysilsesquioxanes, more specifically are one or more of polymethylsilsesquioxane, polyphenylsilsesquioxane, polypropylsilsesquioxane, and polyvinylsilsesquioxane, and most specifically are one or more of polymethylsilsesquioxane, polyphenylsilsesquioxane, and polypropysilsesquioxane.

In an exemplary embodiment of the present invention, the siloxanes are polysiloxanes, more specifically polydimethylsiloxane, polydiphenylsiloxane, polymethylvinylsiloxane, polymethylphenylsiloxane, and most specifically polydimethylsiloxane.

In an exemplary embodiment of the present invention, the silica is one of more of tetramethoxysilane, tetraethoxysilane, tetrakis(methoxyethoxysilane), tetrakis[(methoxyethoxy)ethoxysilane], more specifically tetramethoxysilane or tetraethoxysilane, and most specifically tetramethoxysilane.

In an exemplary embodiment of the present invention, the shell in this invention is silica, hydroxysilica, or titanium dioxide, and more specifically is silica or titanium dioxide.

In an exemplary embodiment of the present invention, the shell in this invention contains 1-30 mol % of silica or 1-10 wt % of titanium dioxide, more specifically 1-20 mol % of silica or 1-7 wt % of titanium dioxide, and most specifically 3-17 mol % of silica or 1-5 mol % of titanium dioxide.

In an exemplary embodiment of the present invention, the water absorbency is 20-80 (g/g) %, and more specifically 25-70 (g/g) %, and most specifically 30-65 (g/g) %.

In an additional aspect of this invention, this invention provides a method for preparing hydrophilic silicone powders that induce formation of units selected from a group consisting of (a) partially hydrolyzed silsesquioxane containing one hydroxyl group (T2) and silica (Q3), (b) partially hydrolyzed silsequioxane containing two hydroxyl groups (T1) and silica (Q3), (c) silica containing three hydroxyl groups (Q1), hydrolyzed silicone containing siloxane (D1), and mixtures thereof.

The method for preparing hydrophilic powders is now described in further details.

According the present invention, the method includes a step to produce hydroxyl group on the surface by hydrolyzing silica, silsesquioxane or siloxane.

According to the method in this invention, the base used may be any base known in the art (i.e. organic base such as amine and inorganic base such as NaOH).

In an exemplary embodiment of the present invention, the base may be NaOH, KOH, Ca(OH)2, Ba(OH)2, CsOH, Sr(OH)2, LiOH, RbOH, Mg(OH)2, triethylamine, or ammonia, more specifically strong inorganic base, and further more specifically NaOH or KOH, and most specifically NaOH.

In an exemplary embodiment of the present invention, the silsesquioxane in this invention is one or more of polysilsesquioxane, more specifically one or more of polymethylsilsesquioxane, polyphenylsilsesquioxane, polypropylsilsesquioxane or polyvinylsilsesquioxane, most specifically one or more of polymethylsilsesquioxane, polyphenylsilsesquioxane, polypropylsilsesquioxane.

In an exemplary embodiment of the present invention, the siloxane in this invention is polysiloxane, more specifically one of more of polydimethylsiloxane, polydiphenylsiloxane or polymethylvinylsiloxane, polymethylphenylsiloxane, and most specifically polydimethylsiloxane.

In an exemplary embodiment of the present invention, the silica in this invention is one or more of tetramethoxysilane, tetraethoxysilane, tetrakis(methoxyethoxysilane), tetrakis[(methoxyethoxy)ethoxysilane], more specifically tetramethoxysilane or tetraethoxysilane, and most specifically tetramethoxysilane.

In an exemplary embodiment of the present invention, the method includes a step of preparing silica, silsesquioxane or siloxane in prior to produce hydroxyl group.

In an exemplary embodiment of the present invention, chlorosilane or organoalkoxysilanes are used as precursors for silica, silsesquioxane, or siloxane, and more specifically organoalkoxysilanes are used.

Examples of alkoxysilane used as precursors for silica in this invention may be tetramethoxysilane and tetraethoxysilane but is not limited thereto.

The alkyltrialkoxysilane used in the present invention as silsesquioxane precursors may be C1-C10 alkyltriC1-C10 alkoxysilane, more specifically C1-C5alkyltriC1-C5alkoxysilane, most specifically C1-C3alkyltriC1-C2alkoxysilane. For example, the alkyltrialkoxysilane in the present invention may be propyltrimethoxysilane, ethyltrimethoxysilane, propyltriethoxysilane, ethyltriethoxysilane, methyltriethoxysilane, but is not limited thereto.

The aryltrialkoxysilane used in the present invention as silsesquioxane precursors may be C5-C10 aryltriC1-C10alkoxysilane, more specifically naphthyltriC1-C5alkoxysilane, most specifically phenyltriC1-C2alkoxysilane. For example, the aryltrialkoxysilane in the present invention may be naphthyltrimethoxysilane, naphthyltriethoxysilane, phenyltrimethoxysilane, phenyltriethoxysilane, but is not limited thereto.

The dialkyldialkoxysilane used in the present invention as siloxane precursors may be diC1-C10dialkylC1-C10dialkoxysilane, more specifically diC1-C5dialkylC1-C5dialkoxysilane, most specifically diC1-C3dialkylC1-C2dialkoxysilane. For example, the dialkyldialkxoysilane in the present invention may be propylmethyldimethoxysilane, ethylmethyldimethoxysilane, dimethyldimethoxysilane, methylpropyldiethoxysilane, diethyldiethoxysilane, or diemethyldiethoxysilane but is not limited thereto.

The arylalkyldialkoxysilane used in the present invention as siloxane precursors may be C5-C10arylC1-C10aklyldiC1-C10alkoxysilane, more specifically phenylC1-C5alkyldiC1-C5alkoxysilane or naphthylC1-C5alkyldiC1-C5alkoxysilane and most specifically phenylmethyldiC1-C2alkoxysilane. For example, the arylalkydialkxoysilane in the present invention may be phenylmethyldimethoxysilane, phenylmethyldiethoxysilane, phenylethyldimethoxysilane or phenylethyldiethoxysilane but is not limited thereto.

The diaryldialkoxysilane used in the present invention as siloxane precursors may be diC5-C10aryldiC1-C10alkoxysilane, more specifically dinaphthyldiC1-C10alkoxysilane, diphenyldiC1-C10alkoxysilane, most specifically diphenyldiC1-C2alkoxysilane. For example, the diaryldialkxoysilane in the present invention may be diphenyldimethoxysilane or diphenyldiethoxysilane but is not limited thereto In an exemplary embodiment of the present invention, the powders in the present invention have 0.1-15 um diameters, and more specifically 0.1-12 um diameters.

In an exemplary embodiment of the present invention, the method includes a step of heating at 60-250° C. after producing hydroxyl group in order to fix hydrophilic components on the surface. More specifically the powders are heated at 60-200° C., more specifically 80-170° C., further more specifically 100-150° C. and most specifically 110-130° C.

In an exemplary embodiment of the present invention, the heat treatment is carried out 10 min-5 hours, more specifically 30 min-4 hours and most specifically 1-3 hours.

In an exemplary embodiment of the present invention, the hydrophilic powders after heat treatment have diameters of 0.1-15 um, and more specifically 0.1-12 um. The particle sizes observed by electron microscope are identical before and after heat treatment.

In another aspect, the present invention provides method for preparing hydrophilic core-shell powders including the following steps, (a) preparing hydrophilic core powder following a method described in the present invention, (b) producing silica, hydroxysilica, and titanium dioxide shell on the surface of the core powder using tetralkoxysilane, titanium tetraalkoxide, and water glass.

The method for preparing hydrophilic core-shell powders is now described in further details.

Step (a) Preparation of Hydrophilic Silicone Core Powder

In accordance with the present invention, one or more of silica, silsesquioxane, and siloxane is hydrolyzed using basic solution to prepare silicone core containing units selected from a group consisting of (a) partially hydrolyzed silsesquioxane containing one hydroxyl group (T2) and silica (Q3), (b) partially hydrolyzed silsesquioxane containing two hydroxyl groups (T1) and silica (Q3), (c) silica containing three hydroxyl groups (Q1), hydrolyzed silicone containing siloxane (D1), and mixtures thereof.

The detailed description for step (a) is omitted because powders prepared by the pre-described method for the preparation of hydrophilic powders are used as cores.

Step (b): Shell Preparation

In completion of step (a), silica, hydroxysilica or titanium dioxide shell are formed by treating the core with tetraalkoxysilane, titanium tetraalkoxide, and water glass.

In an exemplary embodiment of the present invention, tetraalkoxysilane is tetramethoxysilane or tetraethoxysilane, more specifically tetramethoxysilane.

In an exemplary embodiment of the present invention, titanium tetraalkoxide is titanium tetrabutoxide.

As used herein, the term "water glass" is a trivial name for water soluble silicate salt where alkali metal is bonded with silica in different mole ratios. It includes any water glass (i.e. sodium silicate, potassium silicate, and lithium silicate) known in this field.

The method for preparing core and shell have many common aspects and description of common aspects is omitted in order to minimize confusion.

In an exemplary embodiment of the present inventions, the shell is silica, hydroxylsilica, or titanium, more specifically silica or titanium dioxide.

In another aspect, the present invention provides the powders prepared following the method of the present invention.

In another aspect, the present invention provides a composition containing hydrophilic silicone powders and core-shell powders described in this invention, The composition of the present invention may be used for any application where hydrophilic powders may be used. For example, they may be used in cosmetics and medicines, and may be used as lubricants for fibers, rubbers, and leather products.

In an exemplary embodiment of the present invention, the composition is cosmetic composition.

The ingredients included in cosmetic compositions of the present invention are any ingredient that is used in common cosmetic compositions such as stabilizers, solubilizers, vitamins, pigments and fragrances, and media.

The cosmetic composition of the present invention may be any type among solution, emulsion, suspension, paste, gel, creams, lotion, powder, soap, cleansing containing surfactant, oil, powdery foundation, emulsion foundation, was foundation, and spray but is not limited thereto. More specifically, they may be toner, conditioner, conditioning creams, massage cream, essence, eye cream, cleansing cream, cleansing foam, cleansing water, pact, spray, and powders.

For the preparation of paste, cream, cream, and gel in the present invention, animal oil, plant oil, wax, paraffin, starch, tragacanth gum, cellulose derivatives, polyethylene glycol, silicone, bentonite, silica, talc and zinc oxide may be used as media.

For the preparation of powder or spray in the present invention, lactose, talc, silica, aluminum hydroxide, calcium silicate, or polyamine powder may be used as the medium. For sprays, chlorofluorohydrocarbon, propane/butane or dimethyl ether may be used as propellant.

For the preparation of solution or emulsion in the present invention, solvent, emulsifier, or solubilizer is used. For example, water, ethanol, isopropanol, ethyl carbonate, ethyl acetate, benzyl alcohol, benzyl benzoate, propylene glycol, 1,3-butylglycol, glyceryl aliphatic ester, polyethylene glycol or aliphatic acid esters of sorbitol.

For the preparation of suspension in the present invention, water, ethanol, propylene glycol can be used as diluent, ethoxy isostearyl alcohol, polyoxyethylene sorbitol ester, and polyoxyethylene sorbitol esters, microcrystalline cellulose, aluminum metahydroxide, bentonite, agar, tricant may be used.

For the preparation of cleansing that contains surfactants in the present invention, sulfates of aliphatic alcohol, sulfates of aliphatic alcohol ether, sulfonsuccinic monoester, icetionate, imidazolium derivative, methyltaurate, sarcocinate, aliphatic amide ether sulfate, alkylamidobetine, aliphatic alcohol, aliphatic glyceride, diethanol amide of aliphatic acid, plant oil, lanoline derivative or ethoxy glycerol aliphatic esters may be used as a component of the medium.

In an exemplary embodiment of the present invention, the composition is pharmaceutical composition.

For the preparation of pharmaceutical composition in the present invention, the media are those allowed in medicinal regulations.

The media used in the present invention may be lactose, dextrose, sucrose, sorbitol, mannitol, starch, acacia rubber, calcium phosphate, alginate, gelatin, calcium silicate, microcrystalline cellulose, polyvinylpyrolidone, water, syrup, methylcellulose, methylhydroxybenzoate, propylhydroxybenzoate, talc, magnesium stearate, or mineral oil, but is not limited thereto. Pharmaceutical composition in the present invention may contain lubricant, moisturizer, sweetener, flavor, emulsifier, suspension stabilizer, and preserver. Media and allowed ingredients in pharmaceutical composition are listed in Remington's Pharmaceutical Science (19$^{th}$ ed, 1995).

Pharmaceutical compositions in the present invention may be used as both oral and non-oral medication. Non-oral methods include intravenous injection, hypodermic injection, intramuscular injection, abdominal cavity injection, and topical administration.

The appropriate dose of pharmaceutical composition in the present invention may be prescribed according to the preparation method, application method, ages of the patient, weight, gender, medical condition, diet, application time, application path, digestion, and biological reaction. In an exemplary embodiment of the present invention, the daily dose of pharmaceutical composition in this invention is 0.0001-100 mg/Kg.

Pharmaceutical composition in the present invention may be prepared in disposable package or multiple application package after formulated with medically allowed media and/or filler according to common knowledge of those skilled in this art. The formulations may be oil or solution in aqueous media, emulsion, syrup, suspension, extracts, powder, granule, tablet, or capsule, and dispersing agent or stabilizer may be added.

In another aspect, this invention provides w/o and o/w emulsions composed of hydrophilic powders, core-shell powders or powders prepared in the present invention.

As used herein, the term "o/w emulsion" refers to the emulsion where oil is dispersed in water and "w/o emulsion" refers to the emulsion where water is dispersed in oil.

In another aspect, this invention provides the method to prepare o/w or w/o emulsion by mixing hydrophilic powders, core-shell powders or powders prepared in the present invention with oil or water.

The method for the preparation of o/w emulsion and w/o emulsion is as follows.

In accordance with the present invention, hydrophilic powder and core-shell powder in this invention, or powders prepared by the present invention are mixed with water or oil, more specifically with oil.

In an exemplary embodiment of the present invention, oils are cyclopentasiloxane, dimethicone, cetylethylhexanoate, hydrogenated polydecene, or sunflower oil.

In an exemplary embodiment of the present invention, the mixtures are treated by ultrasonic mixer.

EXAMPLES

Example 1

Synthesis of Hydrophilic Silicone Powder Containing T1, T2 Silicon Using Polymethylsilsesquioxane One hundred grams of polymethylsilsesquioxane powders with average diameter of 10 um (N&M Technologies, Inc., Korea), 100 mL of water, and 100 mL of isopropyl alcohol were mixed, and then 20 mL of isopropyl alcohol saturated with KOH was added. The mixture was agitated for 18 hours at room temperature. The powders were recovered by centrifugation and re-dispersed in water. The pH of the mixture was adjusted to 4 using dilute HCl solution. The powders were recovered by centrifugation and washed with excess amount of water. Centrifugation and washing was repeated until the pH of the washing water became above 5. The recovered powder was dried at 160° C.

The amount of recovered powder was 70 g and oil absorbency and water absorbency were Respectively 58 (g/g) % and 56 (g/g) %. Many hydrophilic powders can be wet by oil as a result of capillary act while hydrophobic powders do not absorb water as they do not get wet by water. Accordingly, the water absorbing property of these powders confirm their hydrophilic nature.

The powders feel softer than polymethylsilsesquioxane powders used as the starting material.

TGA analysis carried out in the air at the ramp of 10° C./min to 700° C. showed the original polymethylsilsesquioxane powders lost 9.8% of their weight while treated powders lost 11.83% of their weight. A literature (M A Jun et. al, Chinese Chemical Letters Vol. 13, No. 1 pp. 75-78) reported that pyrolysis product of polymethylsilsesquioxane does not contain any Si—$CH_3$ but consists of $SiO_2$ and $SiC_xO_y$ with unclear structure.

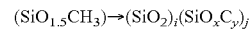

$(SiO_{1.5}CH_3) \rightarrow (SiO_2)_i (SiO_xC_y)_j$

Regardless of the nature of the product, the total amount of Si should be reserved. Therefore, the molecular weight of $(SiO_2)_i(SiO_xC_y)_j$ is the molecular weight of polymethylsilsesquioxane times $(100-0.92)/100$ or $0.902\times 67 = 60.4$ g/mol. The hydrolyzed polymethylsilsesquioxane should be consist mainly of $SiO1.5CH3$ and $SiO_{1.5}(OH)CH_3$ and the formula can be written as $(SiO_{1.5}CH_3)_m[SiO_{1.5}(OH)CH_3]_n$. It is reasonable to consider that heating this product to 700° C. will yield the same product obtained from polymethylsilsesquioxane that was heated to 700° C. Therefore,

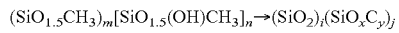

As 11.83% of weight was lost, the molecular weight of $(SiO_{1.5}CH_3)_m[SiO_{1.5}(OH)CH_3]_n$ is as 1.1183 times as the molecular weight of $(SiO_2)_i(SiO_xC_y)_j$ or 60.4 g/mol× 1.1183=67.58 g/mol. m and n are calculated to be m=0.966 and n=0.034. These results indicate there are 3.4% hydrolyzed units in the hydrolyzed product, which is 4.5% by weight.

The assumption in the calculation above is that the hydrolysis caused formation of $SiO_{1.5}(OH)CH_3$ mostly and this is chemically reasonable assumption. There is no available method to detect $SiO_{1.5}(OH)CH_3$ and $SiO_{1.5}(OH)_2CH_3$ separately. $SiO_{1.5}(OH)_2CH_3$ unit might have formed in small amount. The presence of $SiO_{1.5}(OH)_2CH_3$ in the level of 3.4 mol % cannot be analyzed using solid state NMR spectroscopy.

Example 2

Synthesis of Hydrophilic Silicone Powder Containing Q1, Q2, Q3, T1, T2 Silicon

One hundred gram of tetraethoxysilane was mixed into 100 mL of 1:1 mixture of water and isopropyl alcohol. Then 100 mL of HCl solution that was diluted to 20% of its original concentration was added and agitated for 6 hours. One hundred gram of methyltrimethoxysilane was added to the mixture and agitated for 10-60 minutes until the mixture turned opaque. The pH of the reaction mixture was adjusted to 8-9 using 20% NaOH aqueous solution. The mixture was agitated for 18 hours and the pH was adjusted to 11-12 using a concentrated NaOH aqueous solution. The reaction mixture was agitated for 3 hours at 60° C. and the cooled to room temperature and pH was adjusted to 6-7 using dilute HCl solution. The powders were recovered by centrifugation and washed until the pH of the waste water became the same as that of the washing water. Water was removed at room temperature as low as possible and then the powders were dried at 160° C. until the weight loss measured using Ohaus moisture analyzer MB45 (120° C. for 30 minutes) became less than 3%. Most of powders were in the water phase when 10 mg of the powder was mixed with 1 mL of water and 1 mL of hexane, indicating the powders were hydrophilic. The water absorbency of the powders was 43 (g/g) % and the diameters of powders were 2-4 micrometers. Solid state NMR analysis showed that the powder contained 17.3 mol % of silica and 82.7 mol % of methylsilsesquioxane (FIG. 1). The mole % of silica in FIG. 1 was calculated from the ratio between the areas of the peaks from Q silicon and T silicon.

Example 3

Synthesis of Hydrophilic Silicone Powders from Polymethylsilsesquioxane, Polypropylsilsesquioxane Powders A solution of 100 g of methyltriethoxysilane, 20 g of propyltrimethoxysilane, 1200 mL of ethanol, 12 g of n-hexylamine, and 10 g of 10% NaOH aqueous solution was agitated overnight. The pH of the reaction mixture was adjusted to 6-7 and agitated for 5 hours at 80° C. The reaction mixture was cooled to room temperature and the pH was adjusted to 11 using 10% NaOH aqueous solution and the reaction mixture was agitated 6 hours at 60° C. The pH was adjusted to 5-6 using 10% HCl aqueous solution and the powders were recovered by centrifugation. The powders were washed until the pH of the waste water became the same as that of the washing water. The powders were dried at 160° C. until the weight loss became lower than 3%. The weight loss was determined as described in Example 2. The powders were hydrophilic as most powders settled down in the water phases with a little powder at the interface of water and hexane when 10 mg of the powder was mixed with 1 mL of water and 1 mL of hexane. The diameter of the powder was about 4 micrometers and water absorbency was 35%. Solid state NMR showed that the amount of T2 in the treated powder was higher than that in the original powder by 2 mol %. IR spectroscopic analysis also showed that the peak of OH was stronger. These results indicate the formation of T1 and T2 silicon.

Example 4

Synthesis of Hydrophilic Powders by Treating Dimethylsiloxane-Methylsilsesquioxane Powders A solution of 20 g of dimethyldimethoxysilane, 80 g of methyltrimethoxysilane, 1200 mL of ethanol, and 10 g of 10% NaOH aqueous solution was agitated overnight. The pH of the reaction mixture was adjusted to 6-7 and agitated for 5 hours at 80° C. The reaction mixture was cooled to room temperature and the pH was adjusted to 11 using 10% NaOH aqueous solution and the reaction mixture was agitated 6 hours at 60° C. The pH was adjusted to 5-6 using 10% HCl aqueous solution and the powders were recovered by centrifugation. The powders were washed until the pH of the waste water became the same as that of the washing water. The powders were dried at 160° C. until the weight loss became lower than 3%. The weight loss was determined as described in Example 2. The obtained powders were compatible with water, indicating that T3, T2, and D1 silicon were produced.

Example 5

Synthesis of Core-Shell Powders by Treating Dimethylsiloxane-Methylsilsesquioxane Powders A mixture of 10 g of powders obtained in Example 4, 100 mL of 5% aqueous solution of methanol, 1 mL of 10% aqueous NaOH solution, and 5 g of tetramethoxysilane were agitated overnight. The pH was adjusted to 6.5 using 10% HCl aqueous solution and the powders were recovered by centrifugation. The powders were dried at 120° C. until the weight loss became 2.5% at 120° C. The obtained powders had diameters of 2 micrometers and water absorbency was 42%. Solid state NMR analysis showed the content of silica was 15 mol %. The content of silica was calculated as described in Example 2 from the ratio of the total peak areas from D and T silicon, and the peak area from Q silicon.

Water compatibility of the powders and the formation of silica indicated the resulting powders were hydrophilic.

Example 6

Synthesis of Core-Shell Powders with Enhanced Hydrophilicity by Treating Powders Obtained in Example 3

A mixture of 10 g of powders obtained in Example 3, 100 mL of ethanol, 5 g of titanium tetrabutoxide, 5 mL of water, and 1 mL of n-hexylamine was agitated overnight. The powders were recovered by centrifugation and washed with excess amount of ethanol and then water. The powders were dried at 160° C. until the weight loss became less than 3% and then heated at 150° C. for 2 hours. The hydrophilic nature of the powders was confirmed as 10 mg of the powder readily got wet when mixed with 1 mL of water. The powder obtained from Example 3 did not readily get wet but got wet when they were vigorously mixed with water. These results indicated that hydrophilic titanium dioxide formed on the surface of powders obtained in Example 3. The water absorbency of the powders was 60% and ICP-AA (OPTIMA 7300DV, Perkin-Elmer, USA) analysis showed that powders contained 2.3 wt % of titanium, or 2.3(wt %)×(80/48)=3.5 wt % $TiO_2$.

Example 7

Figure 2:
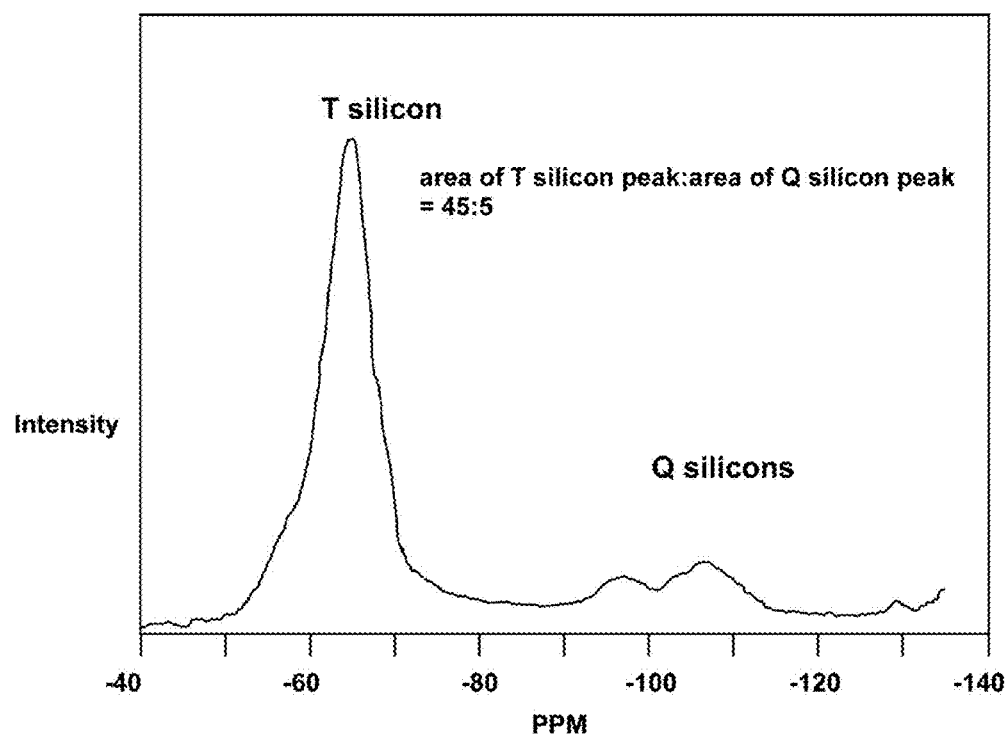
FIG. 2 is a solid state $^{29}$Si NMR spectrum of powder obtained in Example 7.

Synthesis of Core-Shell Powders with Enhanced Hydrophilicity by Treating Hydrolyzed Powders by Water Glass Ten grams of powders obtained in Example 1 was dispersed in 300 mL of water and the pH was adjusted to 9. Ten grams of 30% aqueous solution of sodium silicate was mixed and the mixture was agitated overnight. The powders were recovered by centrifugation and re-dispersed in water and then the pH was adjusted to 5-6. The powders were recovered and dried at 160° C. until the water contents reached about 3%. The powders were heated at 200° C. for 2 hours. The powders readily dispersed in water while the powders obtained in Example 1 dispersed in water only when they were vigorously mixed with water. These results indicated that the treated powders were more hydrophilic. The water absorbency of the powders was 57% and solid state NMR analysis showed that the content of silica was 10 mol % (FIG. 2).

Example 8

Figure 3:
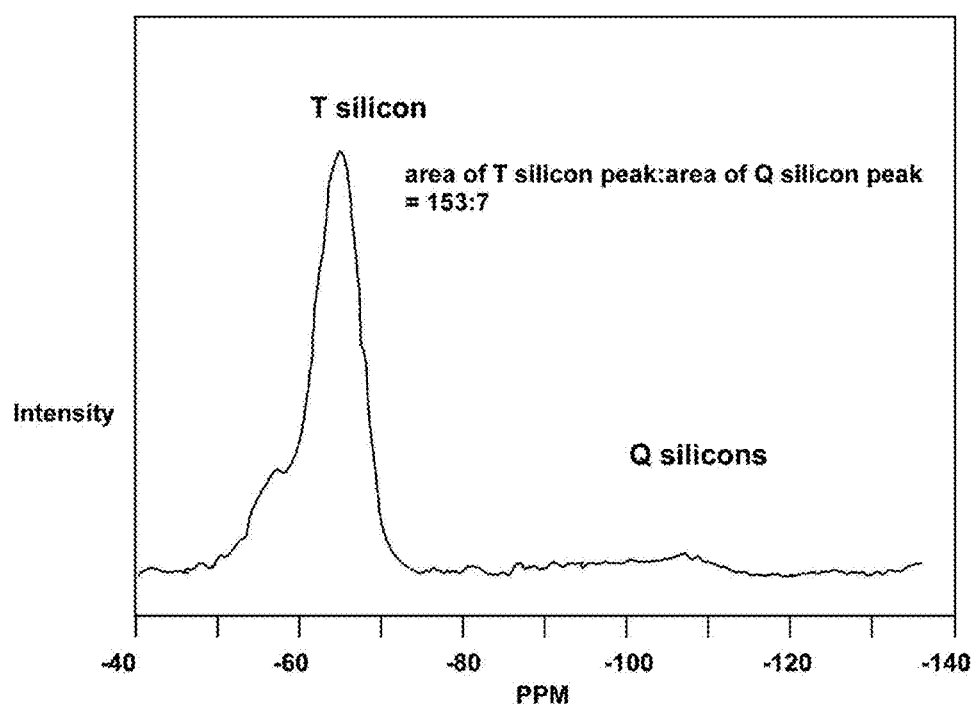
FIG. 3 is a solid state $^{29}$Si NMR spectrum of powder obtained in Example 2.

Synthesis of Core-Shell Powders by Treating Hydrolyzed Polymethylsilsesquioxane by Treating with Tetramethoxysilane One hundred grams of polymethylsilsesquioxane powders with diameter of 5 micrometers (N&M Technologies, Inc., Korea), 100 g of water, 100 mL of isopropyl alcohol, and 10 mL of KOH saturated isopropyl alcohol was agitated for 6 hours at ambient temperature and then the powders were recovered by centrifugation. The powders were re-dispersed in water and the pH was adjusted to 4 using dilute HCl solution. Powders were recovered by centrifugation and washed with water until the pH of waste water became 5. The powders were dried at 160° C. Ten grams of the powder was dispersed in 300 mL of water and the pH was adjusted to 9 and then 3 g of tetramethoxysilane was added. The mixture was agitated overnight. The powder was recovered by centrifugation, re-dispersed in water, and the pH was adjusted to 5-6. The powders were dried at 160° C. until the water content reached about 3% and then heated at 200° C. for 2 hours. The powders readily dispersed in water indication they were hydrophilic. The water absorbency of the powders was 60%. Solid state NMR analysis of Si29 indicated the content of silica was 4.4 mol % (FIG. 3)

Example 9

Thermal Stability of Powders Obtained in Example 7

Five 30 mL vials containing 15 mL of powders obtained in Example 7 were heated respectively at 100, 150, 200, 250, and 300° C. for 6 hours. There was no noticeable changes in color and shape.

Example 10

Figure 4:
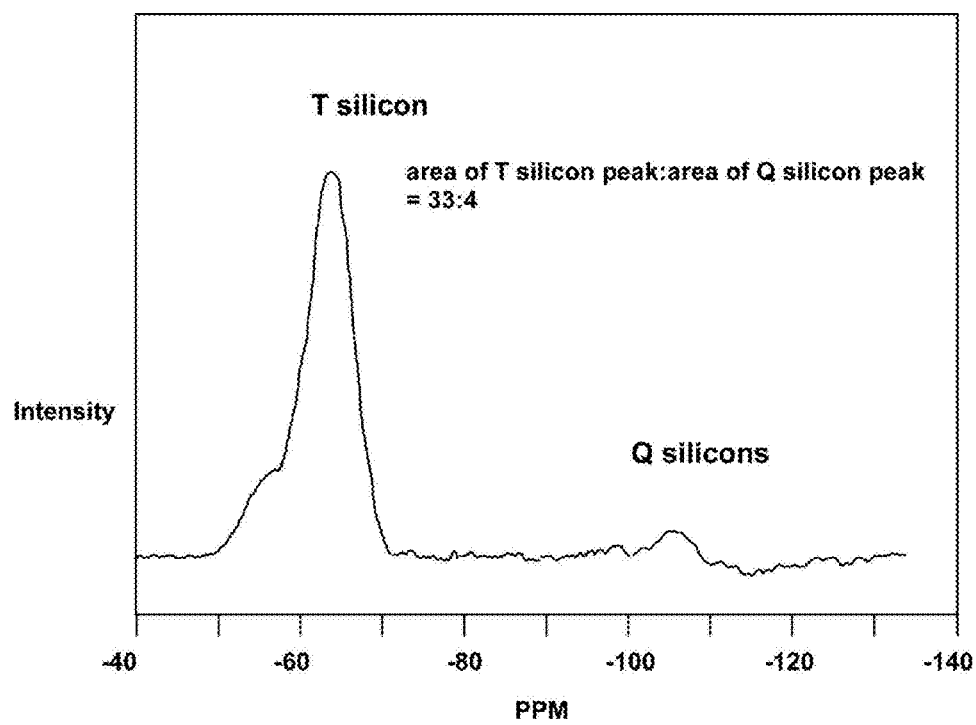
FIG. 4 is a solid state $^{29}$Si NMR spectrum of powder obtained in Example 10.

Synthesis of Hydrophilic Silicone Powders Consisting of Polymethylsilsesquioxane, Polyphenylsilsesquioxane and Silica A mixture of 100 grams of each of methyltrimethoxysilane, phenyltrimethoxysilane, and tetramethoxysilane, 400 mL of water, 1600 mL of ethanol, and 50 mL of trimethylamine was agitated overnight. The pH of the product mixture was adjusted 6-7 using dilute HCl and the powders were recovered by centrifugation. The powders were washed until the pH of the waste water became the same as that of washing water and then re-dispersed in 1000 mL of water. The pH was adjusted to 11.5 using 10% aqueous NaOH solution and agitated vigorously at 60° C. for 6 hours. After cooling to room temperature, the pH was adjusted to 6 and powders were recovered by centrifugation and dried at 160° C. Most powders were in water layer when 10 mg of powder was mixed with 1 mL of water and 1 mL of n-hexane, indicating the powders were hydrophilic. The diameter of the powders was about 2 micrometers. The water absorbency of the powders was 54% and the content of silica was 10.8 mol % (FIG. 4).

Example 11

Comparison of Feelings of the Powders

Ten female testers in twenties applied a small amount of powders on their left arms using their right pointing fingers to evaluate the feelings of different powders by 0 to 10 scale. Polymethylsilsesquioxane powder with 5 micrometer diameter and silica powder with 2 micrometer diameter were used as control for scale 6 and scale 3, respectively. Silkiness, creaminess, and spreadibility were examined and the results are listed in Table 1. The values in Table 1 are averages.

TABLE 1

| Powder | Silkiness | Creaminess | Spreadibility | Average (comparison with polymethylsilsesquioxane) |
|---|---|---|---|---|
| Example 1 | 7.3 | 5.4 | 6.5 | 6.7 (superior) |
| Example 2 | 5.5 | 5.1 | 7.5 | 6.0 (similar) |
| Example 3 | 6.1 | 7.9 | 5.5 | 6.5 (superior) |
| Example 5 | 4.9 | 4.8 | 4.7 | 4.8 (inferior) |

TABLE 1-continued

| Powder | Silkiness | Creaminess | Spreadability | Average (comparison with polymethylsilsesquioxane) |
|---|---|---|---|---|
| Example 7 | 7.5 | 6.4 | 8.5 | 7.5 (superior) |
| Example 8 | 7.2 | 6.7 | 7.0 | 6.9 (superior) |

The results in Table 1 show that powders obtained in Example 7 and Example 8 had much superior feeling than polymethylsilsesquioxane.

Example 12

Minimal Component Creams Using Powders

Eighty grams of virgin coconut oil was melt by heating at 40° C. and 20 grams of powders obtained in Example 1 was mixed. The mixture was homogenized using a portable homogenizer (T. K. homomixer Mark II model 2.5) at 10000 rpm. The obtained mixture had slightly higher viscosity than pure coconut oil but was not sticky when applied on hand. There was no powders observed and felt soft after two hours.

Example 13

Minimal Component Cream Using Powders 2

Mixture of 40 grams of petrolatum and 40 g of linseed oil was melts by heating at 40° C. and 20 grams of powders synthesized in Example 6 was added. The mixture was homogenized using a portable homogenizer (T. K. homomixer Mark II model 2.5). The mixture was homogenized for 5 minutes at 12000 rpm three times with 3 minute interval. The obtained mixture was like wax causing no stickiness or oily feeling but gave smooth touching feeling.

Example 14

Surfactant Like Function of Hydrophilic Powders

Figure 5:
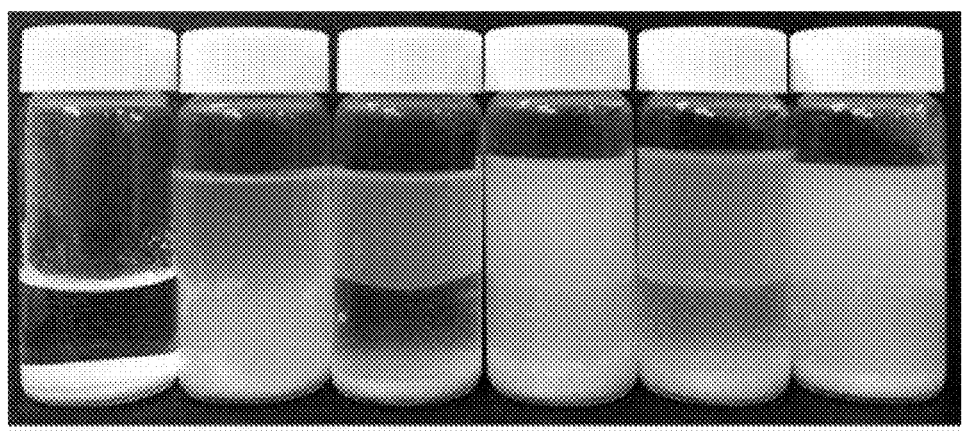
FIG. 5 shows mixtures obtained after sonicating mixtures of 19 parts of oils, 19 parts of water, and 1 part of powder obtained in Example 10 that was wet with water first before mixing. No stable emulsion was produced. The left most vial contains no oil and the oils were cyclopentasiloxane, dimethicone, cetylethylhexanoate, hydrogenated polydecene, and sunflower oil from left to right.
Figure 6:
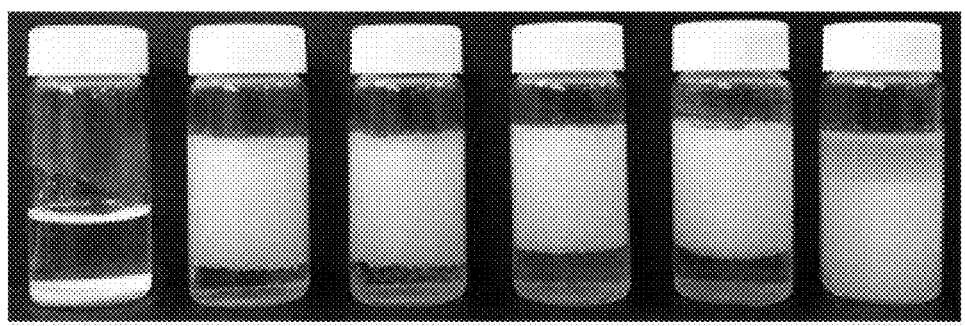
FIG. 6. shows mixtures obtained after sonicating mixtures of 19 parts of oils, 19 parts of water, and 1 part of powder obtained in Example 10 that was wet with oil first before mixing. Stable emulsions were produced. The left most vial contains no oil and the oils were cyclopentasiloxane, dimethicone, cetylethylhexanoate, hydrogenated polydecene, and sunflower oil from left to right.

When 5 g of powders from Example 6 was mixed with 47.5 g of water and 47.5 g of cyclopentasiloxane, dimethicone, cetylethylhexanoate, hydrogenated polydecene, or sunflower oil, and sonicated for 5 minutes (20 W), more powders were found in water layer (FIG. 5). However when the same powders were wet with oil and treated in the same manners, stable emulsions are formed as shown in FIG. 6. Especially the sunflower oil that is more polar than others due to the presence of unsaturated bonds formed w/o emulsion while other less polar oils formed o/w emulsion. The formation of different emulsions may be very useful in formulating new compositions for cosmetic products.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. Hydrophilic silicone particles that contain unit selected from a group consisting of partially hydrolyzed silsesquioxane containing one hydroxyl group (T2) or silica (Q3), partially hydrolyzed silsesquioxane containing two hydroxyl groups (T1) or silica (Q2), hydrolyzed siloxane containing one hydroxyl group (D1), and mixtures thereof in amounts of 1-30 mol % on their surfaces,
   wherein the hydrolyzed siloxane is selected from a group consisting of polydimethylsiloxane, polydiphenylsiloxane, polymethylphenylsiloxane, and mixtures thereof.

2. The particles according to claim 1, wherein the units are produced by hydrolysis in basic conditions.

3. The particles according to claim 1, wherein the silsesquioxanes are selected from a group consisting of polymethylsilsesquioxane, polyphenylsilsesquioxane, polyvinylsilsesquioxane, and mixtures thereof.

4. The particles according to claim 1, wherein silica is produced from precursors selected from a group consisting of tetramethoxysilane, tetraethoxysilane, tetrakis(methoxyethoxysilane), tetrakis[(methoxyethoxy)ethoxysilane], and mixtures thereof.

5. Core-shell particles consisting of hydrophilic silicone particles that contain unit selected from a group consisting of partially hydrolyzed silsesquioxane containing one hydroxyl group (T2) or silica (Q3), partially hydrolyzed silsesquioxane containing two hydroxyl groups (T1) or silica (Q2), hydrolysed siloxane containing one hydroxyl group (D1), and mixtures thereof in amounts of 1-30 mol % on their surfaces as core and silica, and hydroxyl silica titanium dioxide as shell surrounding the core.

* * * * *